United States Patent
Sugiura et al.

(10) Patent No.: US 7,712,368 B2
(45) Date of Patent: May 11, 2010

(54) ULTRASONIC SENSOR HAVING TRANSMISSION DEVICE AND RECEPTION DEVICE OF ULTRASONIC WAVE

(75) Inventors: Makiko Sugiura, Hekinan (JP); Takahiko Yoshida, Okazaki (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 12/314,717

(22) Filed: Dec. 16, 2008

(65) Prior Publication Data

US 2009/0107243 A1   Apr. 30, 2009

Related U.S. Application Data

(62) Division of application No. 11/334,584, filed on Jan. 19, 2006, now Pat. No. 7,540,194.

(30) Foreign Application Priority Data

Mar. 1, 2005   (JP) .............................. 2005-056639

(51) Int. Cl.
*G01S 15/93* (2006.01)
*G01S 7/521* (2006.01)

(52) U.S. Cl. .............................. 73/602; 73/649; 367/99; 367/87; 367/909; 701/301; 701/300; 340/436

(58) Field of Classification Search .................. 73/599, 73/602, 649
See application file for complete search history.

(56) References Cited

U.S. PATENT DOCUMENTS 4,450,430 A * 5/1984 Barishpolsky et al. ...... 340/904
4,581,726 A   4/1986 Makino et al.
4,674,073 A   6/1987 Naruse
4,914,951 A * 4/1990 Koelpin et al. ................. 73/597
6,289,282 B1   9/2001 Hassler et al.
6,381,197 B1   4/2002 Savord et al.
6,492,902 B2   12/2002 Nishimoto et al.
7,420,876 B2   9/2008 Sugiura
2005/0088334 A1   4/2005 Herder
2005/0242596 A1   11/2005 Zanella et al.
2009/0028002 A1 * 1/2009 Sugiura et al. ................. 367/99
2009/0071255 A1 * 3/2009 Okuda et al. ................... 73/628

FOREIGN PATENT DOCUMENTS

EP   1 278 076 A2   1/2003

(Continued)

OTHER PUBLICATIONS

Definition of "capable", Cambridge Dictionary of American English, downloaded Jun. 28, 2009, p. 1.*

(Continued)

*Primary Examiner*—Hezron Williams
*Assistant Examiner*—Rose M Miller
(74) *Attorney, Agent, or Firm*—Posz Law Group, PLC (57) ABSTRACT

An ultrasonic sensor for detecting an object includes: a substrate; a transmission device for transmitting an ultrasonic wave; a plurality of reception devices for receiving the ultrasonic wave; and a circuit for processing received ultrasonic waves, which are received by the reception devices after the ultrasonic wave transmitted from the transmission device is reflected by the object. The transmission device and the reception devices are integrated into the substrate. The dimensions of the sensor are minimized, and detection accuracy of the sensor is improved.

5 Claims, 12 Drawing Sheets

FOREIGN PATENT DOCUMENTS

| | | | |
|---|---|---|---|
| GB | 2112520 A * | 7/1983 | |
| JP | A-61-220598 | 9/1986 | |
| JP | U-H04-057779 | 5/1992 | |
| JP | A-05-292598 | 11/1993 | |
| JP | A-6-331742 | 12/1994 | |
| JP | A-10-013981 | 1/1998 | |
| JP | A-10-20017 | 1/1998 | |
| JP | A-2001-16694 | 1/2001 | |
| JP | A-2003-107156 | 4/2003 | |
| JP | A-2003-284182 | 10/2003 | |
| JP | A-2004-180262 | 6/2004 | |
| WO | WO 2005064589 A1 * | 7/2005 | |

OTHER PUBLICATIONS

Definition of "capable", Webster's New World College Dictionary, 4th edition, downloaded Jun. 28, 2009 from www.yourdictionary.com, pp. 1-3.*

Search Report from French Patent Office issued on Dec. 21, 2006 for the corresponding French patent application No. FR 06 01801 (and English Translation).

Search Report from French Patent Office issued on Dec. 21, 2006 for the corresponding French patent application No. FR 06 01801 ( French language document enclosed).

Office Action mailed May 26, 2009 from the Japanese Patent Office in corresponding Japanese patent application No. 2005-056639 (and English Translation).

* cited by examiner

PRIOR ART

FIG. 13B

PRIOR ART

ULTRASONIC SENSOR HAVING TRANSMISSION DEVICE AND RECEPTION DEVICE OF ULTRASONIC WAVE

CROSS REFERENCE TO RELATED APPLICATIONS

This application is a divisional of U.S. patent application Ser. No. 11/334,584 filed on Jan. 19, 2006, now U.S. Pat. No. 7,540,194, and entitled ULTRASONIC SENSOR HAVING TRANSMISSION DEVICE AND RECEPTION DEVICE OF ULTRASONIC WAVE, and is based on Japanese Patent Application No. 2005-56639 filed on Mar. 1, 2005.

FIELD OF THE INVENTION

The present invention relates to an ultrasonic sensor.

BACKGROUND OF THE INVENTION

An ultrasonic sensor is mounted on an automotive vehicle, for example. The sensor detects a distance between the sensor, i.e., the vehicle and an obstruction when a driver parks the vehicle or when the driver turns the vehicle. The ultrasonic sensor is disclosed in, for example, JP-A-2001-16694. The sensor for detecting the obstruction includes a transmission device and a reception device, which transmits an ultrasonic wave and receives the ultrasonic wave. The sensor may include a transmitting/receiving device. When the transmission device transmits the ultrasonic wave, the ultrasonic wave hits the obstruction. The obstruction reflects the ultrasonic wave; and then, the reflected ultrasonic wave is received by the reception device. On the basis of the received ultrasonic wave by the reception device, an acoustic pressure of the ultrasonic wave, a time lag and/or a phase difference are detected so that a direction to the obstruction and a distance between the obstruction and the vehicle are calculated. Further, a concavity and a convexity of the obstruction can be detected.

The reception device of the ultrasonic wave is for example, an ultrasonic element having a vibrator formed of a piezoelectric thin film disposed on a membrane as a thin portion of a substrate. The ultrasonic element with a membrane structure is disclosed in, for example, JP-A-2003-284182. This element is formed by a micro machining method so that the element is called a MEMS (i.e., micro electro mechanical system) type ultrasonic element. JP-A-2003-284182 also discloses an ultrasonic array sensor including the MEMS type ultrasonic elements.

Figure 13A:
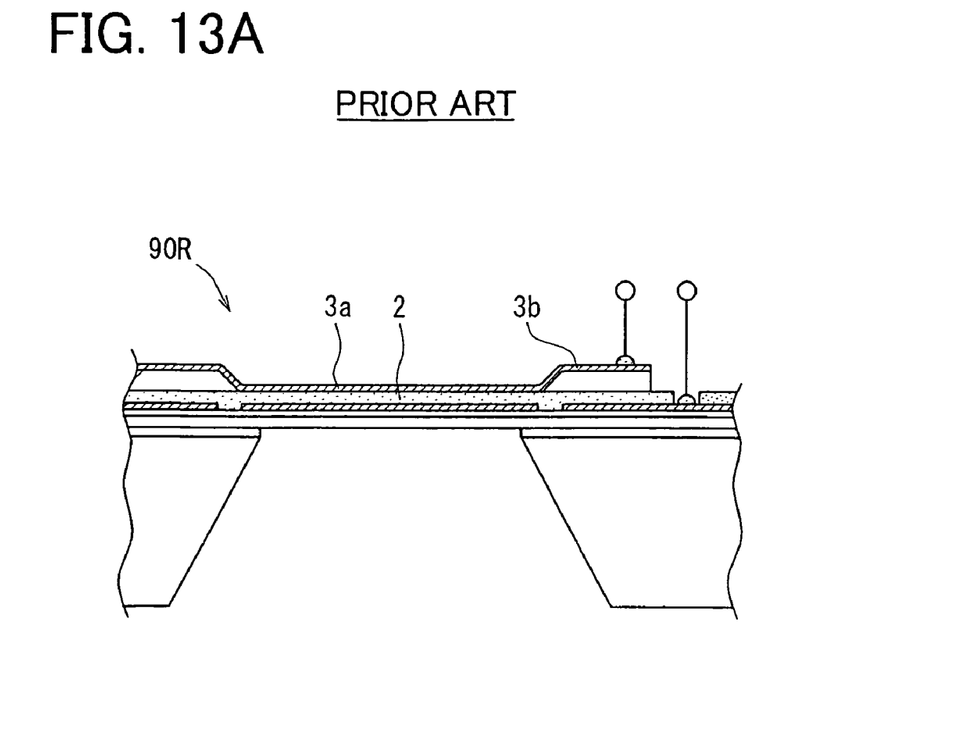
FIG. 13A is a partially enlarged cross sectional view showing an ultrasonic element according to a prior art.

The MEMS type ultrasonic element 90R is shown in FIG. 13A. In the element 90R, a PZT ceramics thin film layer 2 as a ferroelectric substance is sandwiched by a pair of electrodes 3a, 3b. The element 90R further includes a piezoelectric sensor having a predetermined resonance frequency for detecting the ultrasonic wave. When the element 90R operates, a predetermined bias voltage is applied between two electrodes 3a, 3b so that the resonant frequency of the element 90R is changed, i.e., controlled.

Figure 13B:
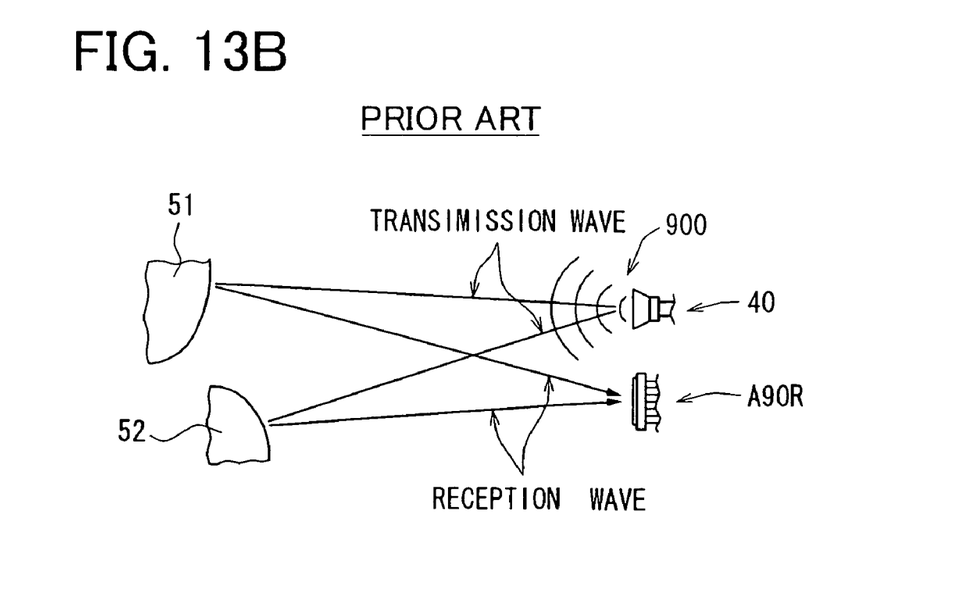
FIG. 13B is a schematic view explaining a method for detecting an object by using an ultrasonic wave, according to the prior art.

FIG. 13B explains a positioning measurement method by using the ultrasonic wave, which is disclosed in JP-A-2003-284182. An ultrasonic sensor 900 includes an ultrasonic wave source 40 as a transmission device of the ultrasonic wave and an ultrasonic array device A90R as a reception device of the ultrasonic wave. The ultrasonic array device A90R includes multiple MEMS type ultrasonic elements 90R, which are arrayed. In the sensor 900, the source 40 is adjacent to the sensing device A90R, and transmits the ultrasonic wave. The ultrasonic wave hits an object 51, 52 as an obstacle; and then, the ultrasonic wave is reflected by the object 51, 52. Thus, the ultrasonic wave is returned to the sensor 900. The returned ultrasonic wave is received by each sensing element 90R in the sensing device A90R. On the basis of the received ultrasonic wave, the position of the object 51, 52 including an orientation angle to the object 51, 52 is determined. Specifically, on the basis of a transmission time of the ultrasonic wave in each incident direction of the sensing element 90R, the distance between the sensing element 90R and the object 51, 52 in the incident direction is calculated. Thus, distribution of the distance in different incident directions is determined. Accordingly, the distance between the object 51, 52 and the sensing element 90R in a depth direction of the object 51, 52 is determined. Here, the transmission time of the ultrasonic wave is a time from a transmission time when the ultrasonic wave is transmitted from the source 40 to a returning time when the ultrasonic wave is returned to the sensing element 90R.

Here, the source 40 and the sensing device A90R are separated each other. Therefore, a manufacturing cost of each of the source 40 and the sensing device A90R is necessitated. Further, when the source 40 and the sensing device A90R are mounted on a bumper of the vehicle, mounting accuracy of each of the source 40 and the sensing device A90R affects detection accuracy of the direction and the distance of the object. Furthermore, the mounting distance between the source 40 and the sensing device A90R may be increased.

Further, in general, when an ultrasonic sensing device is directly mounted on the bumper of the vehicle, the sensing device cannot detect the distance to the object accurately by a water drop or a dust attached on a surface of the sensing element. Furthermore, attenuation of the ultrasonic wave transmitting through air depends on temperature and humidity of the air. These temperature and humidity are changeable in accordance with the environment around the vehicle. Thus, the detection accuracy of the object may depend on temperature change and humidity change. Specifically, the environmental temperature around the vehicle can be detected by an external temperature sensor or the like. However, there is no appropriate external humidity sensor mounted on the outside of the vehicle. Thus, the environmental humidity around the vehicle cannot be detected.

SUMMARY OF THE INVENTION

In view of the above-described problem, it is an object of the present invention to provide an ultrasonic sensor having a transmission device and a reception device of an ultrasonic wave.

An ultrasonic sensor for detecting an object includes: a substrate; a transmission device for transmitting an ultrasonic wave; a plurality of reception devices for receiving the ultrasonic wave; and a circuit for processing received ultrasonic waves, which are received by the reception devices after the ultrasonic wave transmitted from the transmission device is reflected by the object. The transmission device and the reception devices are integrated into the substrate.

The dimensions of the above sensor are minimized, compared with a conventional sensor. Further, a manufacturing cost of the sensor is reduced. Furthermore, a positioning relationship between the transmission device and the reception device is accurately determined; and therefore, detection accuracy of the sensor is not affected by mounting accuracy of the sensor.

Alternatively, the number of the reception devices may be equal to or larger than three so that the circuit is capable of detecting an operation failure. Further, each of the transmission device and the three reception devices has a surface for transmitting or receiving the ultrasonic wave, the surface being perpendicular to a ground. The three reception devices are composed of a first to a third reception devices. The first reception device is disposed above the third reception device, and disposed on a left side of the second reception device. The circuit is capable of calculating a horizontal plane distance between the object and the sensor in a horizontal plane parallel to the ground and a horizontal plane direction angle from the sensor to the object in the horizontal plane on the basis of the received ultrasonic waves received by the first and the second reception devices. The circuit is further capable of calculating a vertical plane distance between the object and the sensor in a vertical plane perpendicular to the ground and a vertical plane direction angle from the sensor to the object in the vertical plane on the basis of the received ultrasonic waves received by the first and the third reception devices. The circuit is capable of checking the horizontal and the vertical plane distances and the horizontal and the vertical plane direction angles on the basis of the received ultrasonic waves received by the second and the third reception devices so that the circuit is capable of detecting the operation failure.

Alternatively, the number of the reception devices may be equal to or larger than four. Further, each of the transmission device and the four reception devices has a surface for transmitting or receiving the ultrasonic wave, the surface being perpendicular to a ground. The four reception devices are composed of a first to a fourth reception devices. The first reception device is disposed above the third reception device, and disposed on a left side of the second reception device. The fourth reception device is disposed under the second reception device, and disposed on a right side of the third reception device. The circuit is capable of calculating a horizontal plane distance between the object and the sensor in a horizontal plane parallel to the ground and a horizontal plane direction angle from the sensor to the object in the horizontal plane on the basis of the received ultrasonic waves received by the first and the second reception devices, and further capable of calculating a vertical plane distance between the object and the sensor in a vertical plane perpendicular to the ground and a vertical plane direction angle from the sensor to the object in the vertical plane on the basis of the received ultrasonic waves received by the first and the third reception devices, so that a first data of the object is obtained. The circuit is capable of calculating the horizontal plane distance and the horizontal plane direction angle on the basis of the received ultrasonic waves received by the third and the fourth reception devices, and further capable of calculating the vertical plane distance and the vertical plane direction angle on the basis of the received ultrasonic waves receive by the second and the fourth reception devices, so that a second data of the object is obtained. The circuit is capable of checking the first data and the second data so that the circuit is capable of detecting the operation failure.

Alternatively, the transmission device may be capable of transmitting multiple ultrasonic waves having different frequencies so that the circuit is capable of compensating humidity. Further, the transmission device is capable of a first ultrasonic wave having a first frequency and a second ultrasonic wave having a second frequency. The number of the reception devices is equal to or larger than three. Each of the transmission device and the three reception devices has a surface for transmitting or receiving the ultrasonic wave, the surface being perpendicular to a ground. The three reception devices are composed of a first to a third reception devices. The first reception device is disposed above the third reception device, and disposed on a left side of the second reception device. The circuit is capable of calculating a horizontal plane distance between the object and the sensor in a horizontal plane parallel to the ground and a horizontal plane direction angle from the sensor to the object in the horizontal plane on the basis of the received ultrasonic waves having the first frequency received by the first and the second reception devices, and further capable of calculating a vertical plane distance between the object and the sensor in a vertical plane perpendicular to the ground and a vertical plane direction angle from the sensor to the object in the vertical plane on the basis of the received ultrasonic waves having the first frequency received by the first and the third reception devices. The circuit is capable of calculating a first attenuation loss between the transmitted ultrasonic wave and the received ultrasonic waves having the first frequency. The circuit is capable of calculating a second attenuation loss between the transmitted ultrasonic wave and the received ultrasonic waves having the second frequency. The circuit is capable of calculating the humidity of environment on the basis of the first and the second attenuation losses and a temperature obtained from an external temperature sensor.

Alternatively, each of the transmission device and the reception devices may be provided by an ultrasonic element. The ultrasonic element is disposed on a membrane of the substrate. The ultrasonic element includes a piezoelectric thin film and a pair of metallic electrodes so that a piezoelectric vibrator is provided. The piezoelectric thin film is sandwiched by the metallic electrodes. The piezoelectric vibrator is capable of resonating together with the membrane at a predetermined ultrasonic frequency. Further, the piezoelectric thin film of the transmission device includes a partial cutting pattern, which is disposed on a stress concentration region of a radial direction vibration of the membrane. Furthermore, the membrane is separated by the partial cutting pattern into four pieces. The membrane has a square planar shape, and each piece of the membrane has a square planar shape. The partial cutting pattern penetrates one of the metallic electrodes and the piezoelectric thin film.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

Figure 1A:
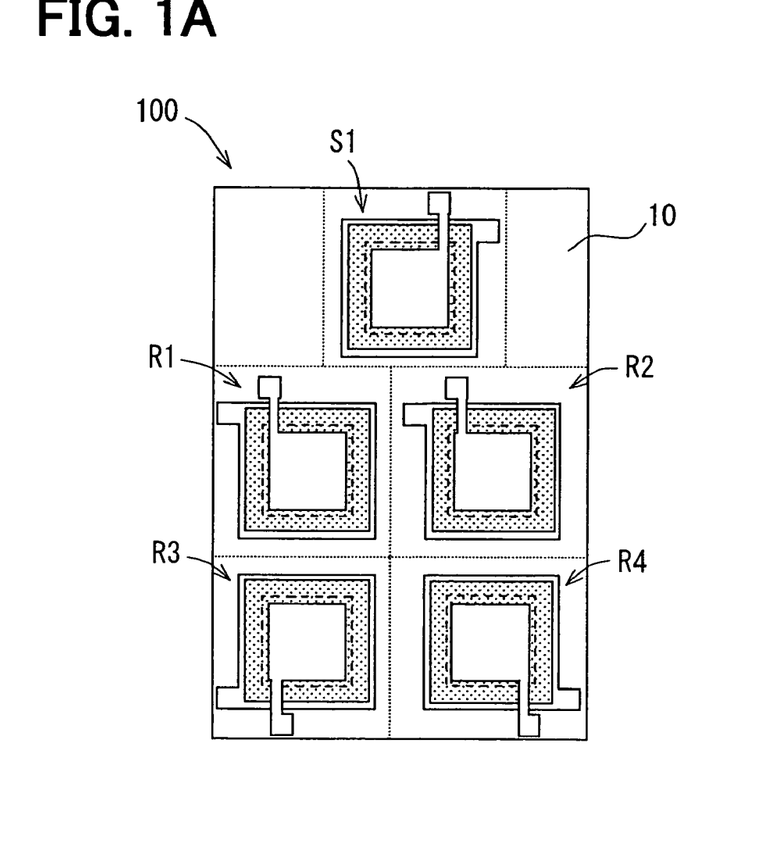
FIG. 1A is a top view showing an ultrasonic sensor according to a preferred embodiment of the present invention.
Figure 1B:
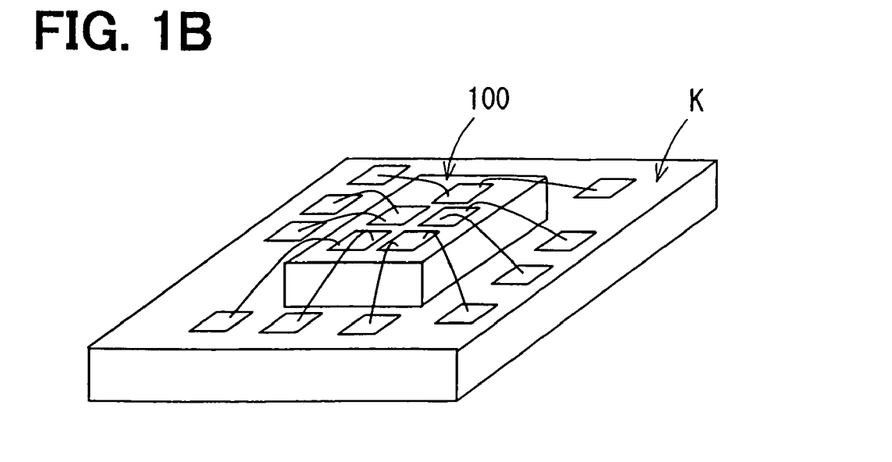
FIG. 1B is a schematic perspective view showing the sensor mounted on a circuit board.
Figure 2A:
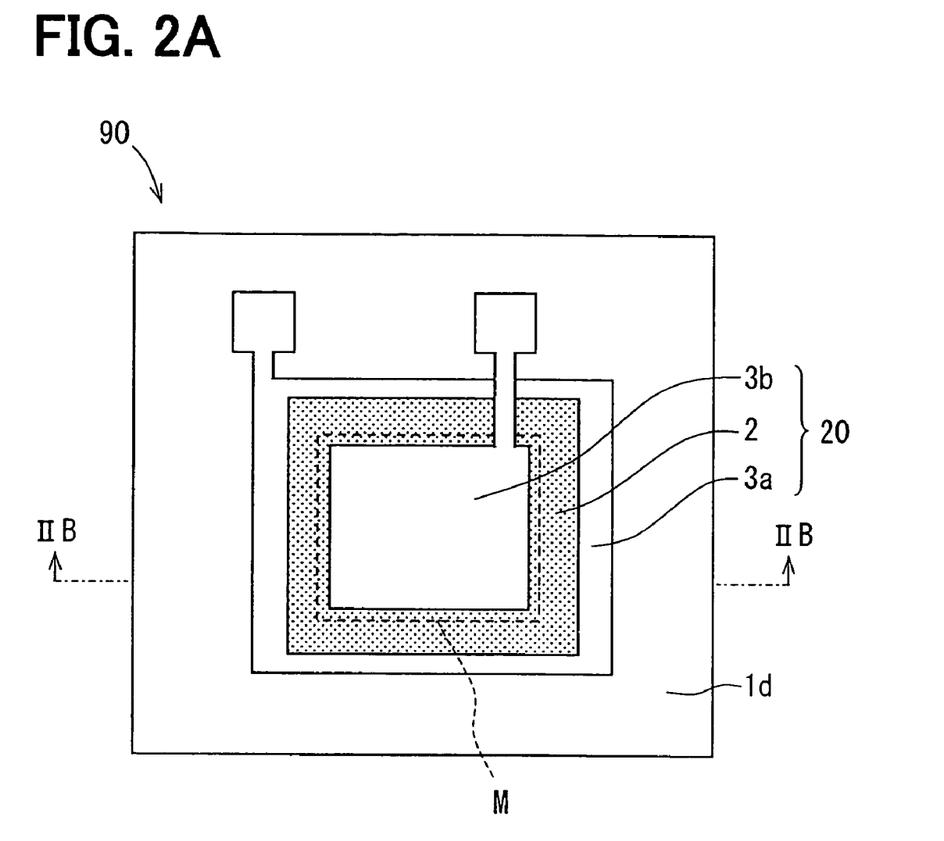
FIG. 2A is a plan view showing an ultrasonic element in the sensor.

An ultrasonic sensor 100 according to a preferred embodiment of the present invention is shown in FIGS. 1A and 1B. FIG. 1B shows the sensor 100 mounted on a circuit board K. The sensor 100 includes one transmission device S1 and four reception devices R1-R4, which are integrated on the same semiconductor substrate 10. FIG. 2A shows an ultrasonic element 90 for providing each of the transmission device S1 and the reception device R1-R4.

The ultrasonic element 90 is similar to the MEMS type ultrasonic element 90R as the reception device shown in FIG. 13A. The transmission device S1 of the ultrasonic element 90 has the same construction of the reception device R1-R4 of the ultrasonic element 90.

Figure 2B:
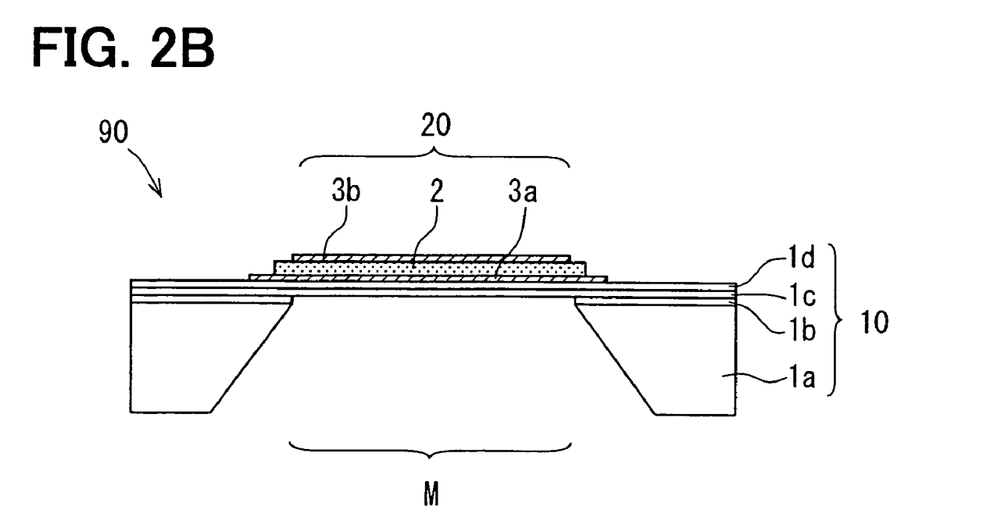
FIG. 2B is a cross sectional view showing the element taken along line IIB-IIB in FIG. 2A.

The ultrasonic element 90 is formed of a SOI (i.e., silicon-on-insulator) semiconductor substrate 10. The substrate 10 includes a first semiconductor layer 1a as a supporting layer, an embedded oxide layer 1b, a second semiconductor layer 1c and a protection oxide film 1d. A membrane M as a thin portion of the substrate 10 is formed by using a semiconductor micromachining method. A piezoelectric vibrator 20 is formed on the membrane M to cover the membrane M. The piezoelectric vibrator 20 includes a piezoelectric thin film 2 and a pair of metallic electrodes 3a, 3b. Specifically, the piezoelectric thin film 2 is sandwiched by a pair of the metallic electrodes 3a, 3b, which are formed of a metallic film.

When the ultrasonic element 90 is used as the transmission device S1, alternating voltage is applied to the metallic electrodes 3a, 3b of the piezoelectric vibrator 20 so that the membrane M together with the piezoelectric vibrator 20 is resonated with a predetermined ultrasonic frequency. Thus, the ultrasonic wave is transmitted. When the ultrasonic element 90 is used as the reception device R1-R4, the returned ultrasonic wave reflected by the object to be measured resonates the membrane M together with the piezoelectric vibrator 20 so that the returned ultrasonic wave is converted to an electric signal by the piezoelectric vibrator 20. Thus, the ultrasonic wave is received.

When the ultrasonic element 90 is used as the transmission device S1, it is preferred that a planar area of the membrane M in the transmission device S1 is comparatively large. This is because it is required to generate large ultrasonic sound pressure outputted from the transmission device S1. Thus, it is preferred that the planar area of the membrane M in the transmission device S1 is larger than that in the reception device R1-R4. Thus, the transmission device S1 can transmit the ultrasonic wave having large sound pressure. However, the planar area of the membrane M in the reception device R1-R4 may be comparatively small as long as the reception device R1-R4 has sufficient sensitivity of the ultrasonic wave.

Figure 3:
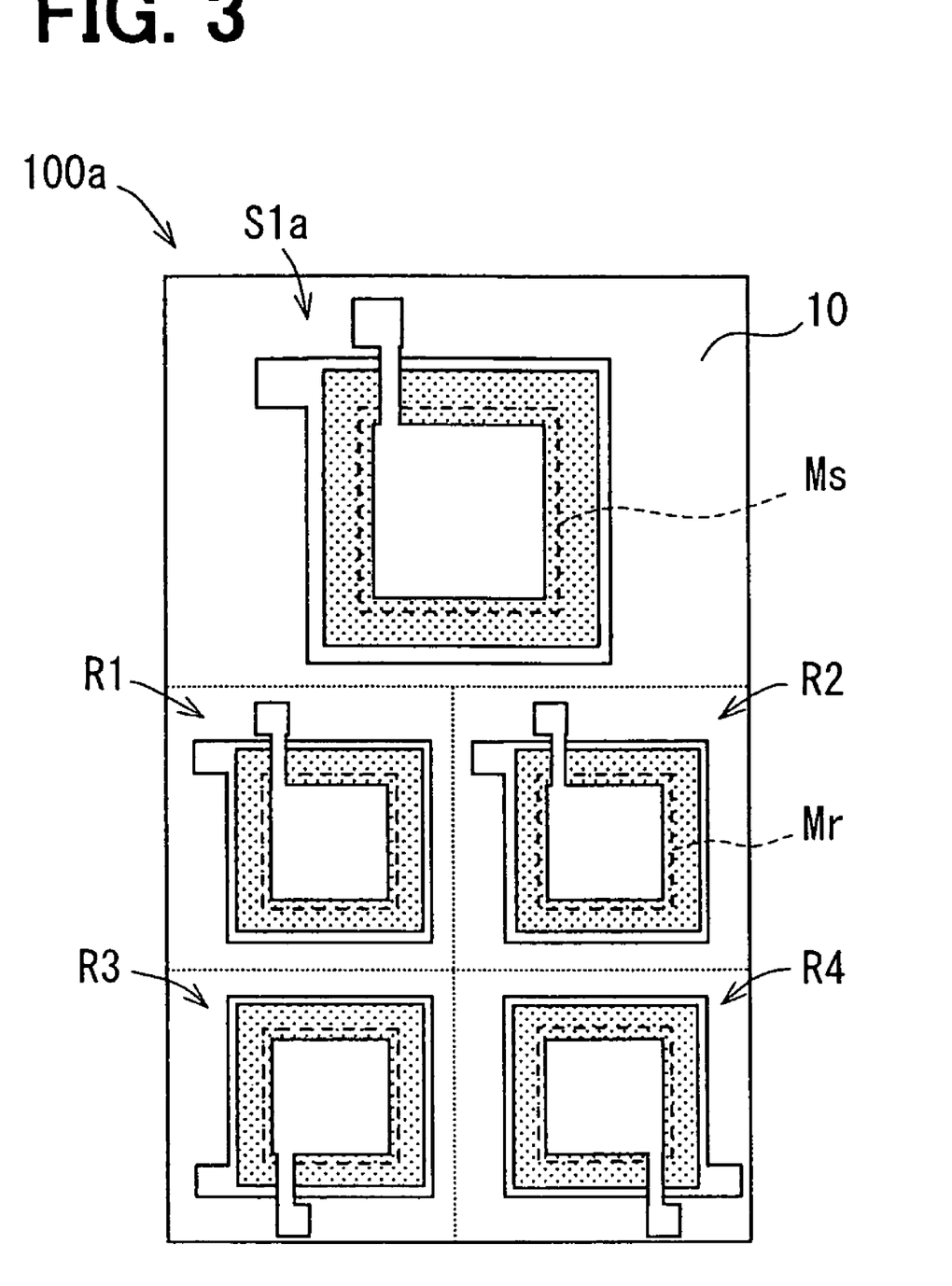
FIG. 3 is a plan view showing another ultrasonic sensor, according to a modification of the embodiment.

FIG. 3 shows another ultrasonic sensor 100a according to the preferred embodiment of the present invention. In this case, the planar area of the membrane Ms in the transmission device S1a is larger than the planar area of the membrane Mr in the reception device R1-R4.

FIGS. 4A to 8C show other ultrasonic elements 91-95 for using as the transmission device S.

Figure 4A:
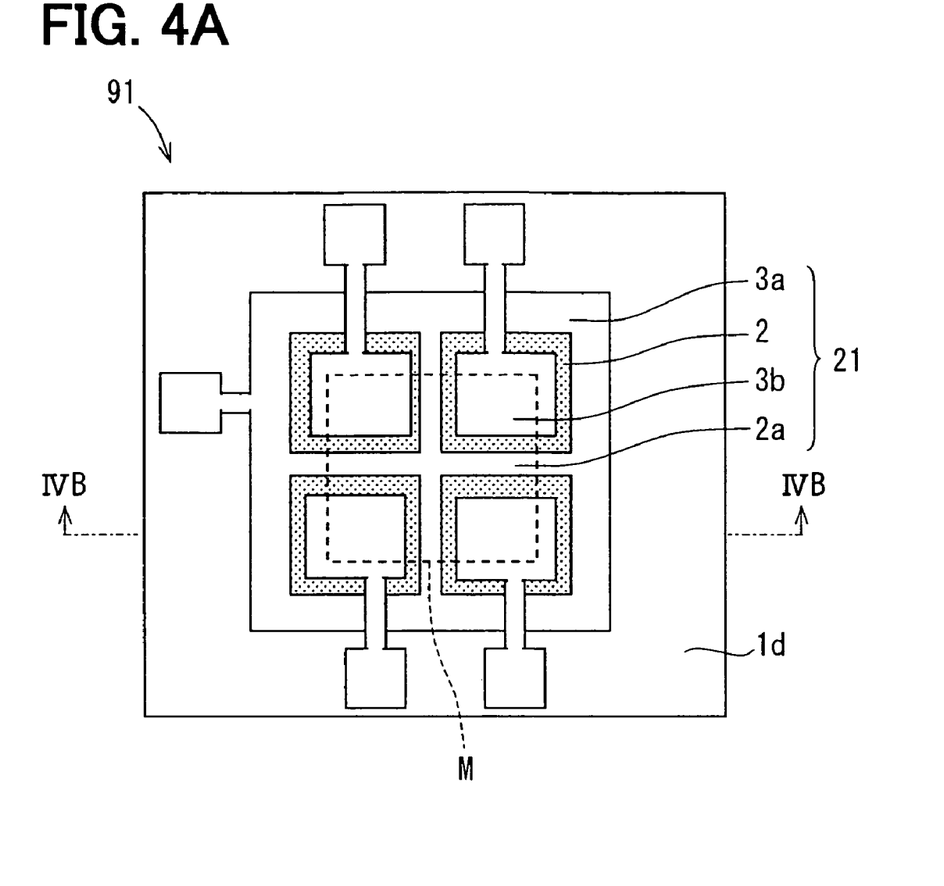
FIG. 4A is a plan view showing an ultrasonic element according to a second modification of the embodiment.
Figure 4B:
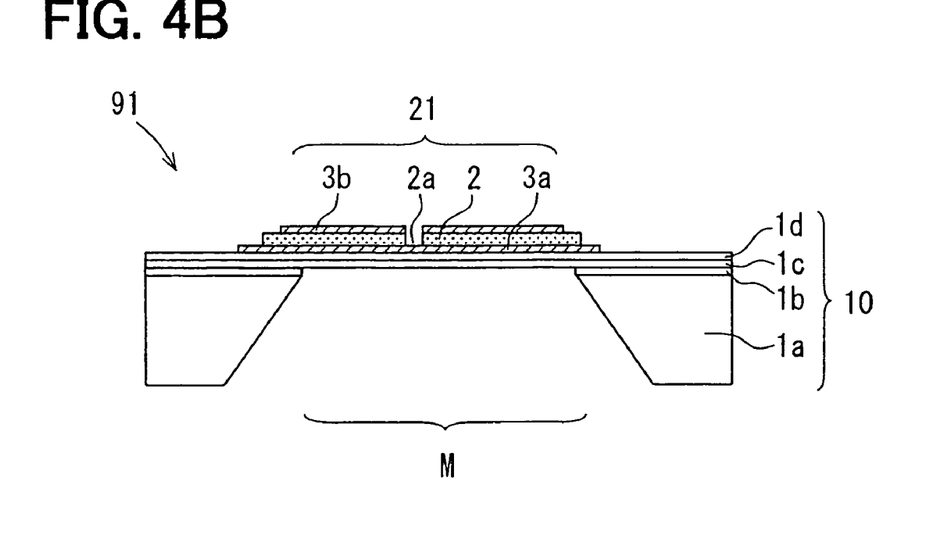
FIG. 4B is a cross sectional view showing the element taken along line IVB-IVB in FIG. 4A.

The ultrasonic element 91 shown in FIGS. 4A and 4B includes the semiconductor substrate having SOI structure. The piezoelectric vibrator 21 is formed on the membrane M formed to be a thin portion of the substrate 10. The piezoelectric vibrator 21 covers the membrane M. The piezoelectric vibrator 21 also includes the piezoelectric thin film 2 and the metallic electrodes 3a, 3b. The piezoelectric thin film 2 is sandwiched by the metallic electrodes 3a, 3b.

In the piezoelectric vibrator 21 of the ultrasonic element 91, the piezoelectric thin film 2 includes a partial cutting pattern 2a as a groove, which separates the piezoelectric thin film 4 into four parts. This partial cutting pattern 2a is obtained by removing a part of the piezoelectric thin film 2, at which a stress caused by radial direction vibration of the membrane M is concentrated. Therefore, rigidity of the part of the piezoelectric thin film 2 as a stress concentration region is reduced, so that the membrane M is easily bent, i.e., the flexibility of the membrane M is increased. Accordingly, the piezoelectric vibrator 21 can transmit, i.e., output the ultrasonic wave having sufficient sound pressure.

Figure 5A:
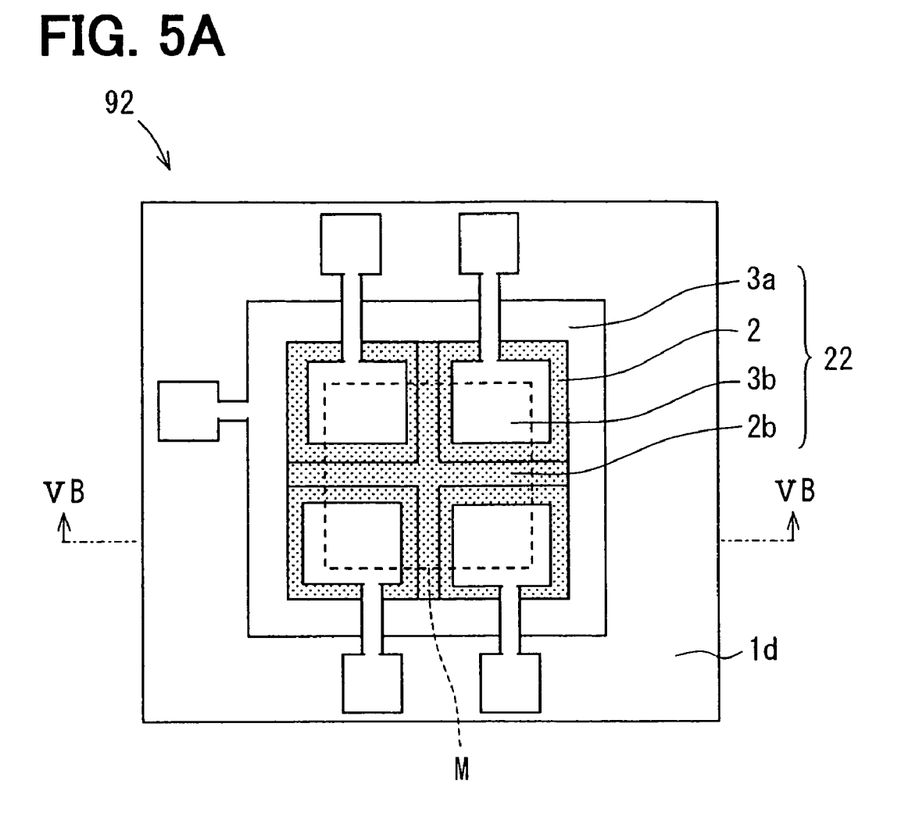
FIG. 5A is a plan view showing an ultrasonic element according to a third modification of the embodiment.
Figure 5B:
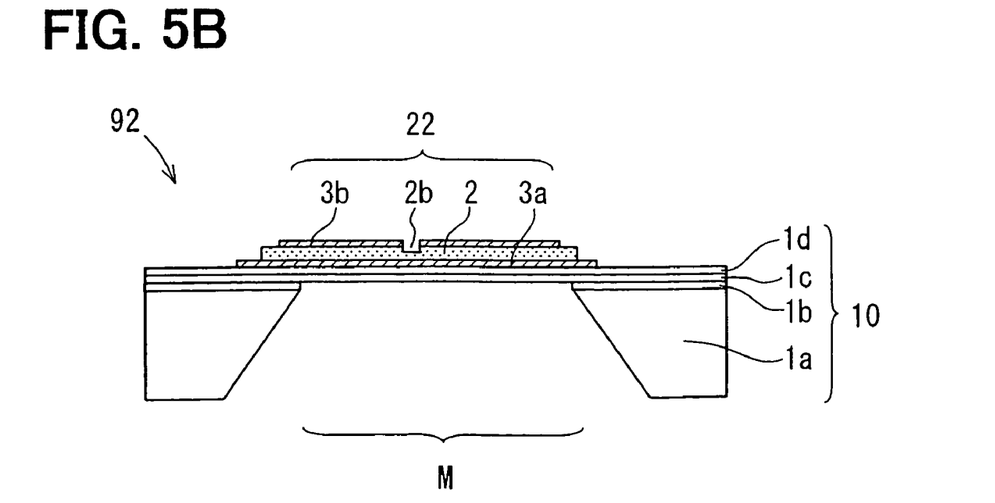
FIG. 5B is a cross sectional view showing the element taken along line VB-VB in FIG. 5A.

In the piezoelectric vibrator 22 of the ultrasonic element 92 shown in FIGS. 5A and 5B, the piezoelectric thin film 2 includes a partial concavity pattern 2b as a partial groove. The thickness of the part of the piezoelectric thin film 2, which is the stress concentration region of the radial direction vibration of the membrane M, is reduced so that the partial concavity pattern 2b is formed. Thus, the flexibility of the membrane M is increased so that the piezoelectric vibrator 21 can output the ultrasonic wave having sufficient sound pressure.

Figure 6A:
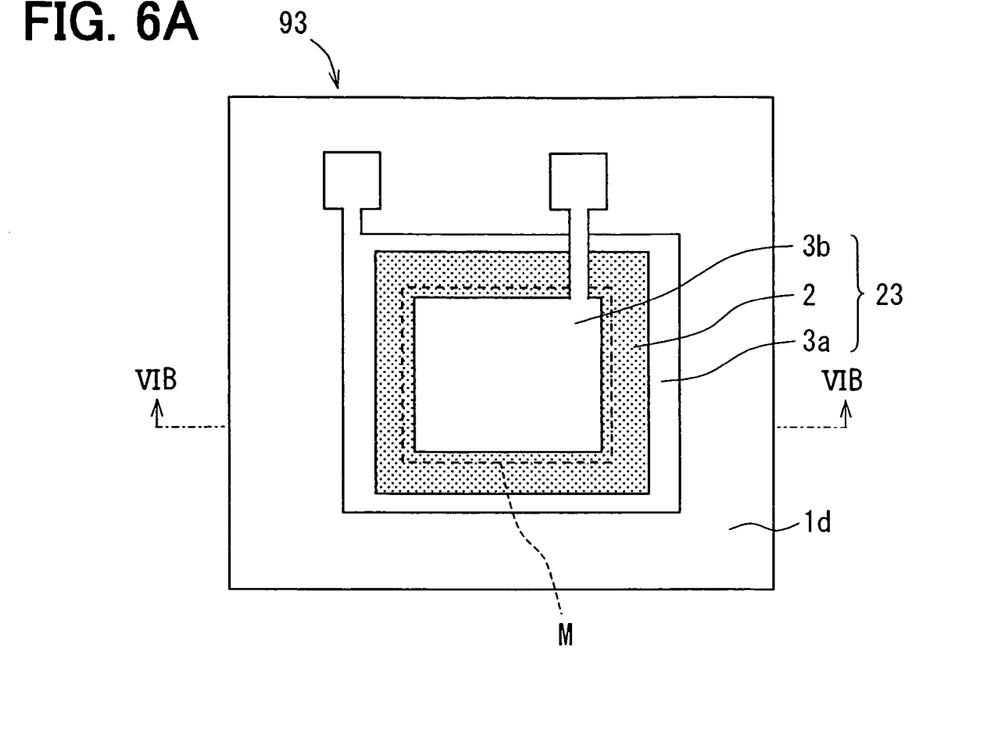
FIG. 6A is a plan view showing an ultrasonic element according to a fourth modification of the embodiment.
Figure 6B:
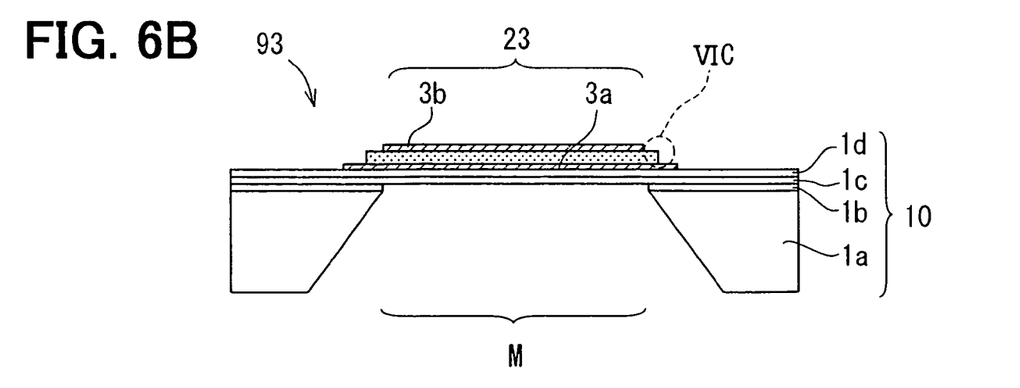
FIG. 6B is a cross sectional view showing the element taken along line VIB-VIB in FIG. 6A.
Figure 6C:
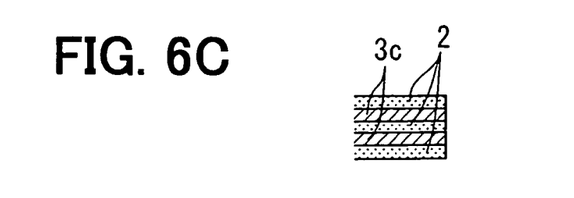
FIG. 6C is a partially enlarged cross sectional view showing a part VIC of the element in FIG. 6B.

The piezoelectric vibrator 23 of the ultrasonic element 93 shown in FIGS. 6A to 6C is formed of multiple layers composed of multiple piezoelectric thin films 2 and multiple metallic electrodes 3a-3c, which are alternately stacked. When the voltage is applied to the piezoelectric vibrator 23, deformation of the piezoelectric vibrator 23 is increased. Thus, vibration amplitude of the membrane M is increased so that the vibrator 23 outputs the ultrasonic wave having sufficient sound pressure.

Figure 7A:
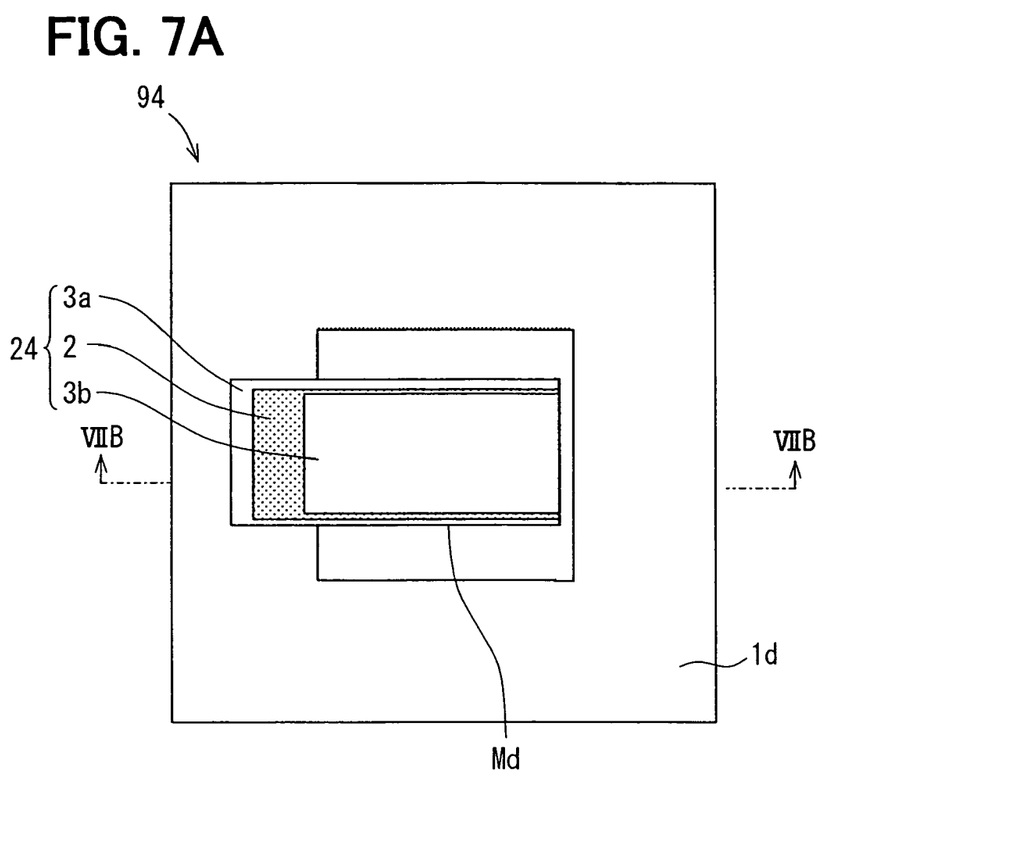
FIG. 7A is a plan view showing an ultrasonic element according to a fifth modification of the embodiment.
Figure 7B:
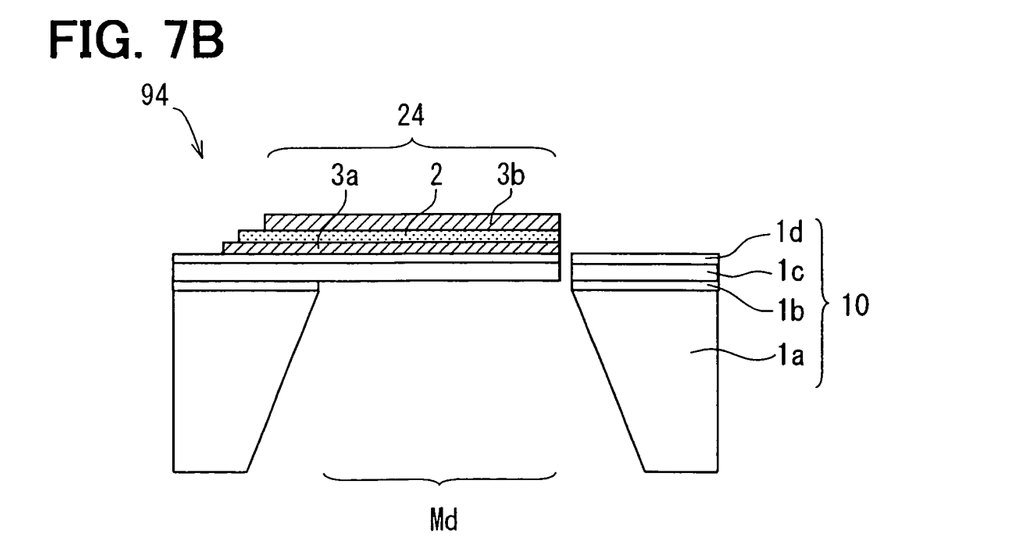
FIG. 7B is a cross sectional view showing the element taken along line VIIB-VIIB in FIG. 7A.

In the piezoelectric vibrator 24 of the ultrasonic element 94 shown in FIGS. 7A and 7B, the piezoelectric vibrator 24 and the membrane Md are cantilevered with the substrate 10. Thus, the membrane Md can be deformed sufficiently, i.e., no portion of the membrane Md, which prevents the membrane Md from deforming, exists in the membrane Md. Thus, when the voltage is applied to the piezoelectric vibrator 24 so that the piezoelectric vibrator 24 is deformed, the membrane Md is also deformed largely. Accordingly, the vibrator 24 outputs the ultrasonic wave having sufficient sound pressure.

Figure 8A:
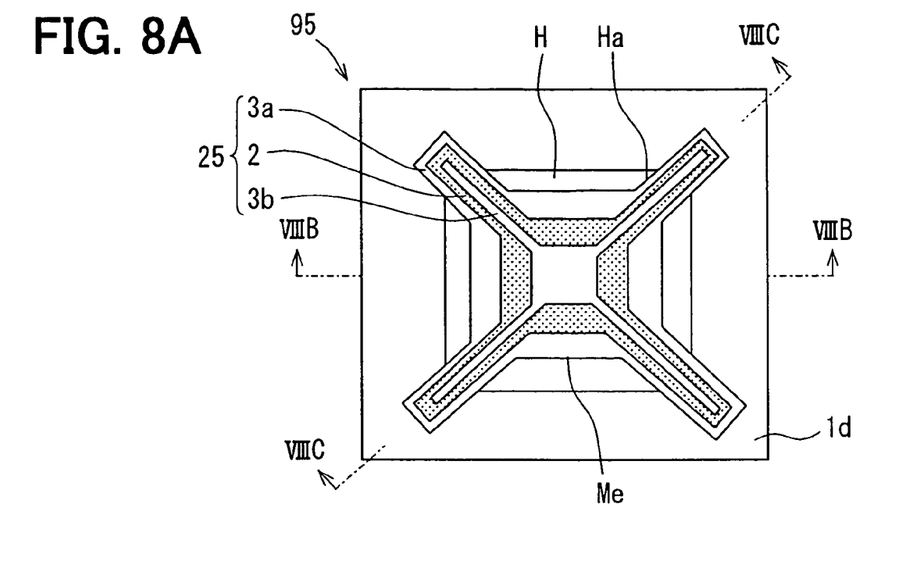
FIG. 8A is a plan view showing an ultrasonic element according to a sixth modification of the embodiment.
Figure 8B:
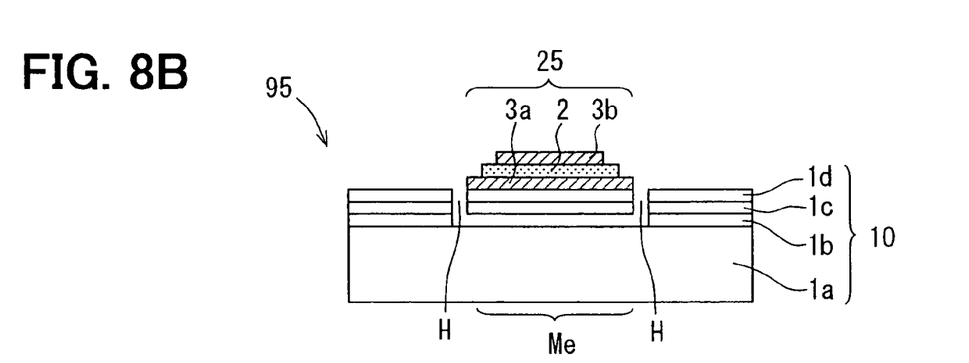
FIG. 8B is a cross sectional view showing the element taken along line VIIIB-VIIIB in FIG. 8A.
Figure 8C:
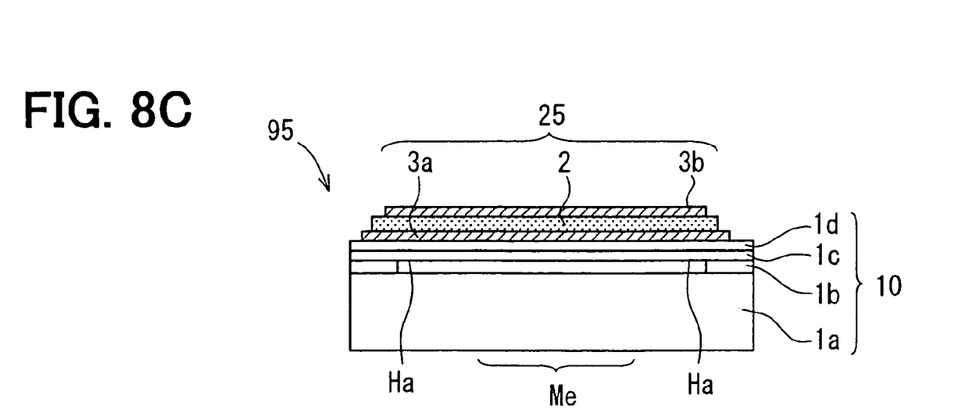
FIG. 8C is a cross sectional view showing the element taken along line VIIIC-VIIIC in FIG. 8A.

In the piezoelectric vibrator 25 of the ultrasonic element 95 shown in FIGS. 8A to 8C, the membrane Me is formed in such a manner that a part of the embedded oxide layer 1b of the substrate 10 is hollowed, i.e., cut from a top surface side of the substrate 10 by a sacrifice etching method. A hole H for the sacrifice etching method is formed around the membrane Me and a beam Ha. Accordingly, the periphery of the membrane Me is partially supported on the substrate 10 through the beam Ha. Thus, the interference part of the membrane Me, which prevents the membrane Me from deforming, becomes small. When the voltage is applied to the piezoelectric vibrator 25 so that the membrane Me is deformed, distortion of the beam Ha is generated and the beam Ha is deformed largely; and therefore, the membrane Me is largely deformed. Thus, the vibrator 25 outputs the ultrasonic wave having sufficient sound pressure.

Since each ultrasonic element 91-95 can output the ultrasonic wave having sufficient sound pressure, the element 91-95 can provide the transmission device S1 of the ultrasonic sensor 100 having high detection accuracy. Here, the element 91-95 may also provide the reception device R1-R4 of the ultrasonic sensor 100.

Figure 9A:
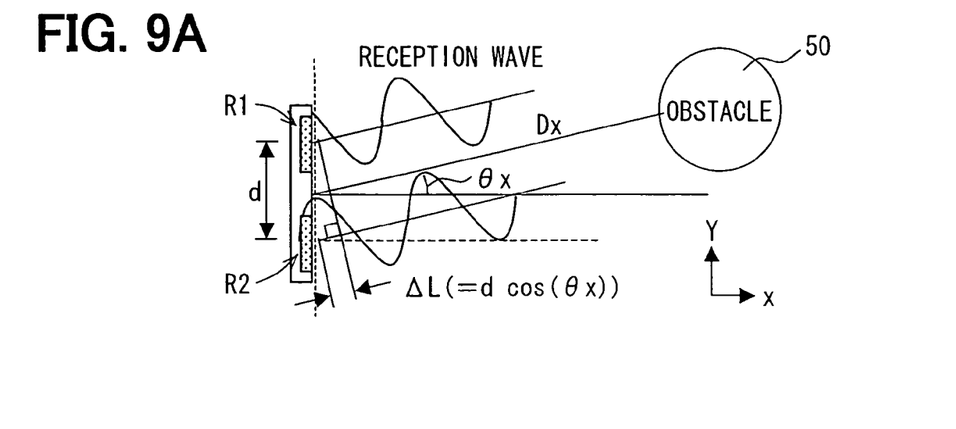
FIG. 9A is a schematic view explaining a reception ultrasonic wave in a X-Y plane received by reception devices.
Figure 9B:
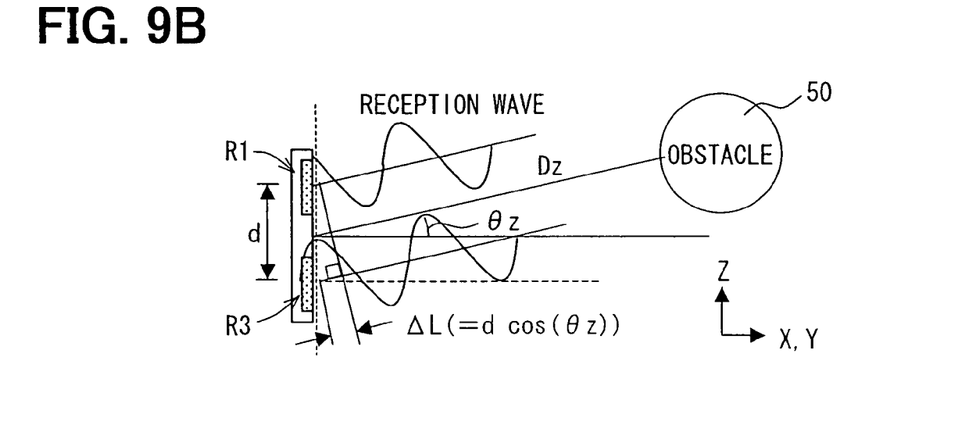
FIG. 9B is a schematic view explaining the reception ultrasonic wave in a Z plane received by the reception devices.
Figure 9C:
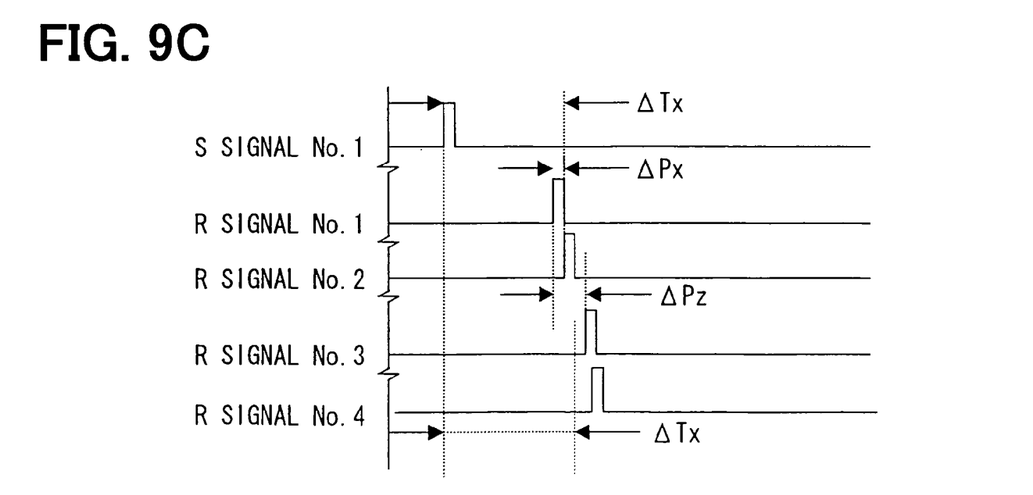
FIG. 9C is a timing chart showing signals from a transmission device and four reception devices.

Next, a method for detecting the object by using the ultrasonic sensor 100 is explained with reference to FIGS. 9A to 9C. In FIGS. 9A to 9C, the substrate surface of the ultrasonic sensor 100 is disposed to be perpendicular to the ground. Specifically, the surface of the transmission device S1 is perpendicular to the ground. Here, a X-Y plane in FIG. 9A is parallel to the ground. A Z-axis in FIG. 9B is perpendicular to the ground. FIG. 9A shows the reception devices R1, R2 of the ultrasonic sensor 100 and the reception ultrasonic wave in the X-Y plane. Specifically, the ultrasonic wave transmitted from the transmission device S1 is reflected by the obstacle 50, and then the reflected ultrasonic wave is received by the reception device R1, R2 as the reception ultrasonic wave. FIG. 9B shows the reception devices R1, R3 of the ultrasonic sensor 100 and the reception ultrasonic wave in the Z-X, Y plane. Here, the Z-X, Y plane in FIG. 9B is perpendicular to the ground. ΔL represents difference of a path of the reception ultrasonic wave. FIG. 9C is a timing chart showing an alternate pulse signal of the ultrasonic wave outputted from the transmission device S1 and four alternate pulse signals of the ultrasonic wave received by four reception devices R1-R4.

In FIG. 9A, Dx represents a distance between the center of the ultrasonic sensor 100 and the obstacle 50 in the X-Y plane. The distance Dx is calculated on the basis of a S signal No. 1 outputted from the transmission device S1, a R signal No. 1 received by the reception device R1 and a R signal No. 2 received by the reception device R2. The reception devices R1, R2 are disposed on an upper side of the sensor 100 in FIG. 1. Specifically, the distance Dx is calculated from an average time difference ΔTx between reception times (i.e., an arrival time) of the R signals No. 1 and No. 2 and a transmission time (i.e., an output time) of the S signal No. 1.

In FIG. 9A, θx represents a direction angle to the obstacle 50 in the X-Y plane. The direction angle θx is measured from the X-axis as a reference axis. The direction angle θx is obtained on the basis of the R signals No. 1 and No. 2 from the reception devices R1 and R2. Specifically, the direction angle θx is calculated from a phase difference ΔPx between the R signal No. 1 and the R signal No. 2.

In FIG. 9B, Dz represents a distance between the center of the ultrasonic sensor 100 and the obstacle 50 in the Z-X, Y plane, which is perpendicular to the ground. The distance Dz is calculated on the basis of the S signal No. 1 from the transmission device S1, the R signal No. 1 from the reception device R1 and a R signal No. 3 received by the reception device R3. The reception devices R1, R3 are disposed on a left side of the sensor 100 in FIG. 1. Specifically, the distance Dz is calculated from an average time difference ΔTz between reception times of the R signals No. 1 and No. 3 and the transmission time of the S signal No. 1.

In FIG. 9B, θz represents a direction angle to the obstacle 50 in the Z-X, Y plane. The direction angle θz is measured from the X-Y plane as a reference plane. The direction angle θz is obtained on the basis of the R signals No. 1 and No. 3 from the reception devices R1 and R3. Specifically, the direction angle θz is calculated from a phase difference ΔPz between the R signal No. 1 and the R signal No. 3.

On the basis of the distances Dx, Dz and the direction angles θx, θz, the distance between the obstacle 50 and the sensor 100 and the direction to the obstacle 50 are determined. Thus, the sensor 100 detects the obstacle 50.

In the sensor 100, the transmission device S1 and the reception devices R1-R4 are integrated into the same substrate 10. Accordingly, the dimensions of the sensor 100 and the manufacturing cost of the sensor 100 are reduced, compared with the sensor 900 shown in FIG. 13B, in which the transmission device S1 and the ultrasonic allay device A90R are independently formed. Further, since the positioning relationship between the transmission device S1 and the reception device R1-R4 is accurately designed, i.e., determined on the substrate 10. Thus, even when the sensor 100 is mounted on a bumper of an automotive vehicle, mounting accuracy of the sensor 100 on the bumper does not affect the detection accuracy of the sensor 100.

Even when the number of the transmission devices S1 and/or the number of the reception devices R1-R4 are increased or reduced, and/or even when the dimensions of the transmission device S1 and/or the dimensions of the reception device R1-R4 are changed, the sensor 100 can be formed only by changing a mask. Thus, the manufacturing cost of the sensor 100 is almost the same.

Although the sensor 100 includes four reception devices R1-R4, the obstacle 50 can be detected by using three reception devices R1-R3. Specifically, the distance Dx in the X-Y plane and the direction angle θx measured from the X-axis are obtained by using two reception devices R1, R2, which are disposed on the upper side of the sensor 100. The distance Dz in the Z-X, Y plane and the direction angle θ z measured from the X-Y plane are obtained by using two reception devices R1, R3, which are disposed on the left side of the sensor 100.

However, the distance Dx in the X-Y plane and the direction angle θx measured from the X-axis can be obtained by using two reception devices R3, R4, which are disposed on a lower side of the sensor 100. The distance Dz in the Z-X, Y plane and the direction angle θz measured from the X-Y plane can be obtained by using two reception devices R2, R4, which are disposed on the right side of the sensor 100. Thus, the obstacle 50 can be detected by three reception devices R2-R4.

Accordingly, in the sensor 100, two different distances and two different direction angles to the obstacle 50 are obtained. By comparing these two data of the obstacle 50, operation failure of the sensor 100 is judged. Specifically, when two data of the obstacle do not coincide, the operation failure of the sensor 100 occurs. Accordingly, the sensor 100 has operation failure detection function.

If the sensor 100 determines that only one reception device R1-R4 acts up the operation failure, the sensor 100 can detect the obstacle 50 by using other three reception devices R1-R4. Accordingly, the sensor 100 has fail safe function.

Further, even when the sensor 100 includes only three reception devices R1-R3, the sensor 100 can have the operation failure detection function. Specifically, the distance Dx and the direction angle θx are obtained from two reception devices R1, R2, and the distance Dz and the direction angle θz are obtained by using two reception devices R1, R3. Accordingly, the obstacle 50 is detected on the basis of two combination data, one of which is obtained from the reception devices R1, R2, and the other one of which is obtained from the reception devices R1, R3. The other combination data obtained from the reception devices R2, R3 can be used for checking the calculation of detection of the obstacle 50. Thus, even when the sensor 100 includes three reception devices R1-R3, the sensor 100 can have the operation failure function.

Thus, when the sensor 100 includes three or more reception devices R1-R3, the sensor 100 has the operation failure function. When the sensor 100 includes four or more reception devices R1-R4, the sensor 100 has the fail safe function. Thus, if the operation failure of the sensor 100 is occurred by waterdrop or dust, which is attached to the sensor 100, the sensor 100 can avoid the operation failure.

The sensor 100 can output two or more different ultrasonic waves having different frequencies, which are transmitted from one transmission device S1 by controlling the frequency of the alternate pulse signal in terms of time, the pulse signal being applied to the transmission device S1. By using two different ultrasonic waves, the sensor 100 can detect the obstacle 50 with humidity compensation function. Here, the input voltage is controlled to have a frequency range other than the resonant frequency of the membrane M so that the ultrasonic waves having two different frequencies are transmitted.

Figure 10:
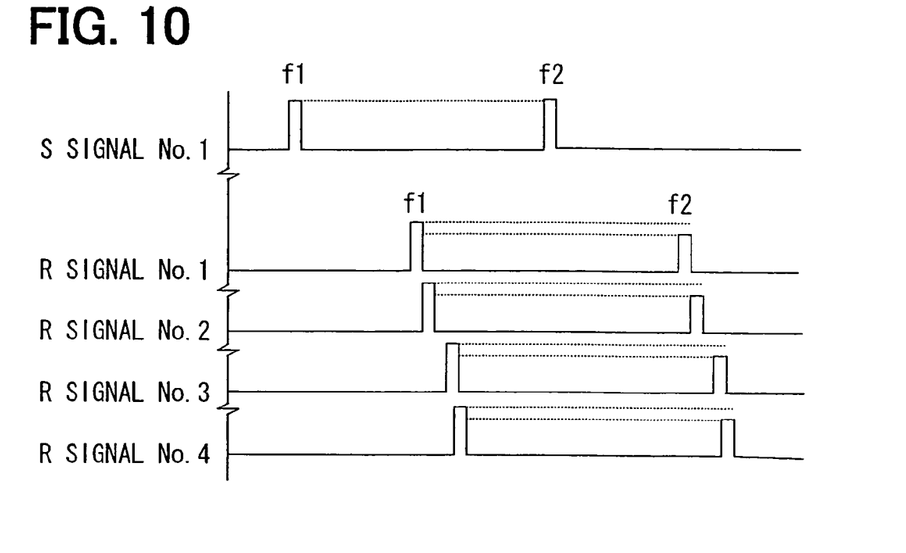
FIG. 10 is a timing chart showing signals having two different frequencies from a transmission device and four reception devices, according to a seventh modification of the embodiment.

FIG. 10 explains the method for compensating the humidity. In FIG. 10, the transmission device S1 outputs two different ultrasonic waves having two different frequencies f1, f2. The transmission device S1 transmits the first ultrasonic wave having the first frequency f1, and then, the device S1 transmits the second ultrasonic wave having the second frequency f2. The first and the second ultrasonic waves are periodically, i.e., with a predetermined time interval, outputted. In four reception devices R1-R4, the first R signal No. 1 corresponding to the first ultrasonic wave and the second R signal No. 1 corresponding to the second ultrasonic wave to the first R signal No. 4 corresponding to the first ultrasonic wave and the second R signal No. 4 corresponding to the second ultrasonic wave are detected. The relationship among the first R signals No. 1-4 and the first S signal No. 1 corresponding to the first ultrasonic wave in FIG. 10 is the same as that in FIG. 9C. Further, the relationship among the second R signals No. 1-4 and the second S signal No. 1 corresponding to the second ultrasonic wave in FIG. 10 is the same as that in FIG. 9C.

In FIG. 10, the height of the alternate pulse signal of the first S signal No. 1 of the first frequency f1 is equal to that of the second S signal No. 1 of the second frequency f2. However, the height of the first R signal No. 1 of the first frequency f1 is higher than that of the second frequency f2, i.e., the second R signal No. 1 of the second frequency f2 is largely attenuated, compared with the first R signal No. 1 of the first frequency f1. Similarly, the second R signals No. 2-4 are largely attenuated, i.e., reduced.

Here, attenuation loss P, i.e., absorption loss of the ultrasonic wave is obtained by the following formula.

$$P \propto e^{-mr} \tag{F1}$$

$$m = (33 + 0.2T)f^2 \times 10^{-12} + \frac{Mf}{k/2\pi f + 2\pi f/k} \tag{F2}$$

$$k = 1.92 \times \left(\frac{G_0}{G} \times h\right)^{1.3} \times 10^5 \tag{F3}$$

Here, m represents absorption coefficient, r represents transmission distance, M represents a predetermined coefficient, f represents a frequency, T represents a temperature, $G_0$ represents a saturated vapor pressure, G represents a total air pressure, and h represents a humidity.

From the above formula F1, the attenuation loss P depends on the frequency f. As the frequency f of the ultrasonic wave becomes larger, the attenuation loss becomes larger. Further, the attenuation loss P depends on not only the frequency but also the temperature T and the humidity h of the transmission environment. The frequency f of the ultrasonic wave is preliminarily determined. The temperature T of the environment can be detected by an external temperature sensor or the like. When the sensor 100 is mounted on the vehicle, the temperature T, i.e., the external temperature can be detected easily. However, the humidity h of the environment, i.e., the external humidity h is not detected easily by a humidity sensor. This is because there is no appropriate humidity sensor for detecting the external humidity around the vehicle.

However, since the received ultrasonic waves having two different frequencies f1, f2 are measured, the humidity h can be calculated on the basis of the difference of two attenuation losses P obtained from two different frequencies f1, f2. This calculated humidity h is used for compensating the standard humidity, which is preliminarily determined and memorized in the sensor 100. Thus, the sensor 100 has the humidity compensation function. In this case, the detection accuracy of the sensor 100 is much improved regarding the humidity change.

Although the sensor 100 includes only one transmission device S1, it is preferred that the sensor 100 includes two or more transmission devices S1. When the sensor 100 includes two transmission devices S1, each transmission device S1 can output the ultrasonic wave having different frequency with high Q value, the device S1 outputting the wave by using different resonant frequency of the membrane M.

Figure 11A:
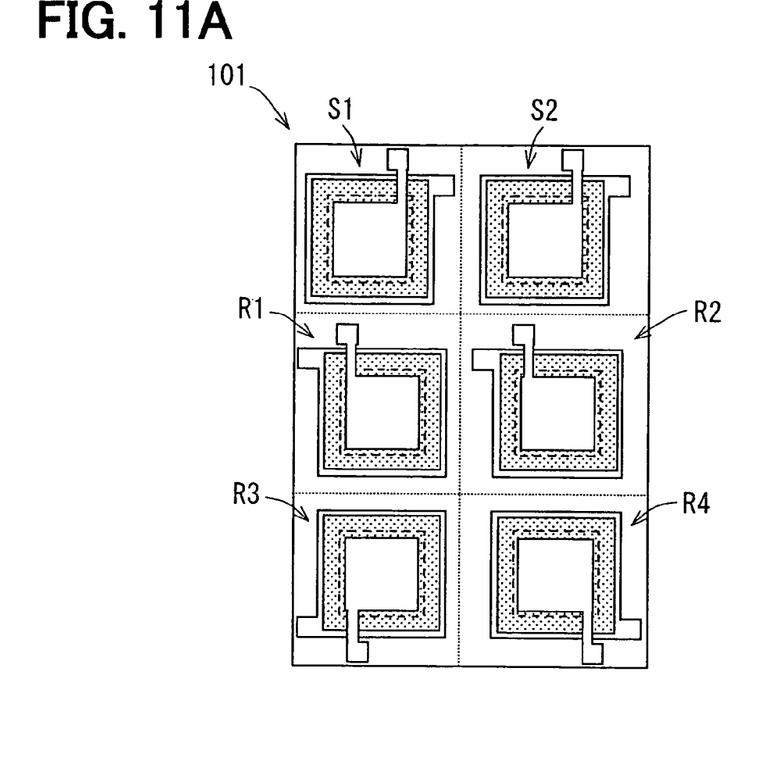
FIG. 11A is a top view showing an ultrasonic sensor according to an eighth modification of the embodiment.
Figure 11B:
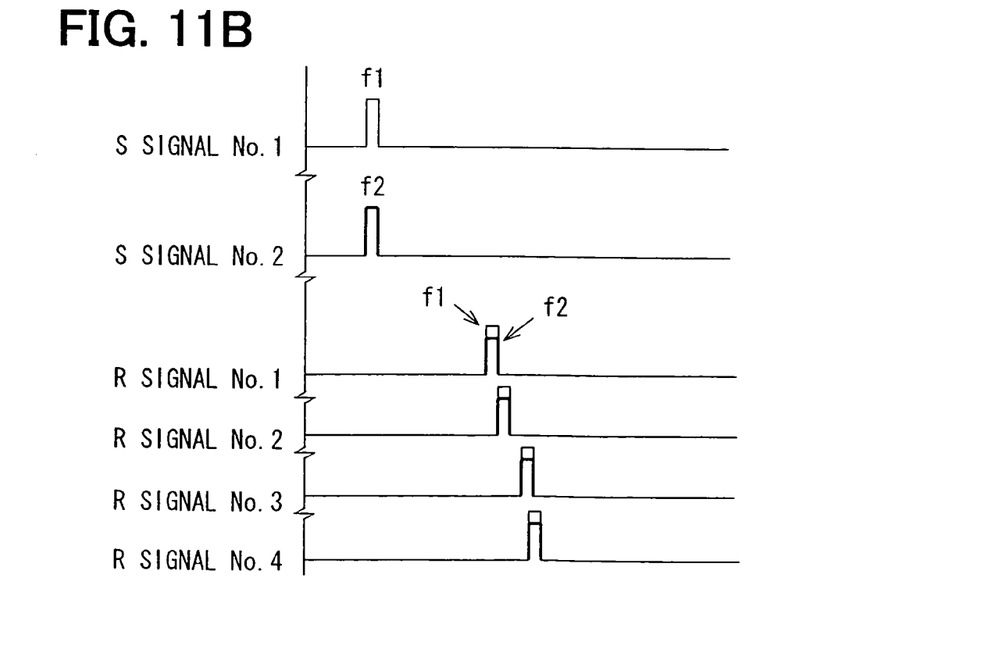
FIG. 11B is a timing chart showing signals having two different frequencies from two transmission devices and four reception devices, according to the eighth modification.

FIG. 11 shows an ultrasonic sensor 101 having two transmission devices S1, S2. The sensor 101 can output two ultrasonic waves having different frequencies f1, f2 simultaneously by using two transmission devices S1, S2 for outputting two different ultrasonic waves. Thus, no compensation for compensating motion of the vehicle is necessitated. Here, since the ultrasonic waves having different frequencies f1, f2 have the same transmission velocity, the reflected ultrasonic waves are arrived at the sensor 100 at the same time. Accordingly, frequency analysis for decomposing the reception ultrasonic waves into the component having the first frequency f1 and the component having the second frequency f2 is required.

Figure 12:
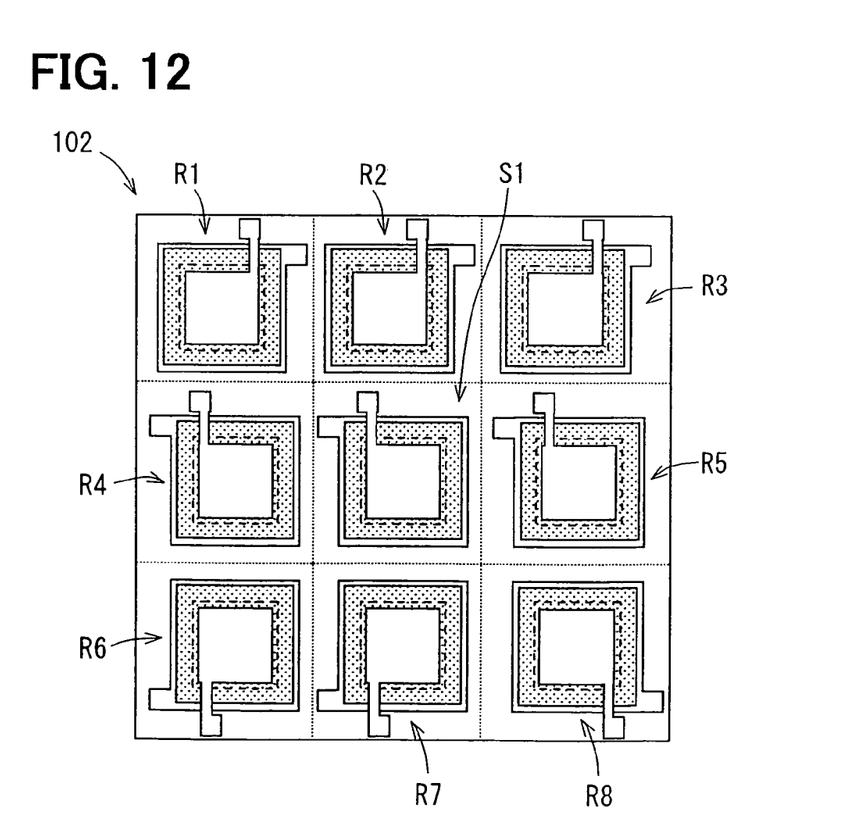
FIG. 12 is a top view showing an ultrasonic sensor according to a ninth modification of the embodiment.

FIG. 12 shows an ultrasonic sensor 102 having the transmission device S1 and eight reception devices R1-R8. The transmission device S1 is surrounded with eight reception devices R1-R8. In this case, it is preferred that two reception devices R1-R8 are arranged to be symmetrically with respect to the transmission device S1. Specifically, a pair of the reception devices R1, R8, a pair of the reception devices R2, R7, a pair of the reception devices R3, R6, and a pair of the reception devices R4, R5 are arranged to be symmetrically with respect to the transmission device S1 so that each pair of the reception devices R1-R8 surrounds the transmission device S1.

In this case, since each pair of the reception devices R1-R8 is symmetrically disposed, the reflected ultrasonic wave outputted from the transmission device S1 is returned to the pair of the reception devices R1-R8 in such a manner that the sound pressure of the received ultrasonic wave received by one of the pair of the reception devices R1-R8 is almost the same as the other one of the pair of the reception devices R1-R8. Accordingly, the detection accuracy of the obstacle 50 is improved.

Thus, each sensor 100, 100a, 101, 102 has small dimensions and low manufacturing cost, and the detection accuracy of the sensor 100, 100a, 101, 102 is not affected by mounting accuracy of the sensor on the vehicle. Further, the sensor 100, 100a, 101, 102 has high detection accuracy, even if the waterdrop or the dust is adhered to the sensor 100, 100a, 101, 102 and even if the humidity around the sensor 100, 100a, 101, 102 changes.

Although the sensor 100, 100a, 101, 102 includes one transmission device S1 and four or eight reception devices R1-R8, the sensor may includes one or more transmission devices S1 and two or more reception devices. When the sensor includes multiple transmission devices and multiple reception devices, the information from the sensor is increased. Further, when the sensor includes two or more transmission devices, the sound pressure of the ultrasonic wave becomes larger, and the directivity of the ultrasonic wave is controlled.

Alternatively, the reception devices in the sensor may be arrayed so that a transmission signal is received by multiple reception devices in order to cancel the transmission signal, since the transmission signal may cause noise of the sensor. Specifically, when the transmission device and the reception device are integrated into one substrate, the transmission signal may input into the reception device so that the transmission signal may cause the noise of the sensor. Thus, by canceling the inputted transmission signal, the noise of the sensor is reduced. Accordingly, when the obstacle is disposed near the sensor, the S/N ratio of the signal is improved for detecting the obstacle.

Although the reception device includes the piezoelectric thin film so that the reception device provides a piezoelectric type device, the reception device may be a capacitance type device for detecting a capacitance change between electrodes. Further, the reception device may be a piezo type for detecting an output of a gauge generated by pressure. Furthermore, the sensor may include a combination of these different type reception devices.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. An ultrasonic sensor for detecting an object, comprising:
a substrate;
a transmission device for transmitting an ultrasonic wave;
a plurality of reception devices for receiving the ultrasonic wave; and
a circuit for processing received ultrasonic waves, which are received by the reception devices after the ultrasonic wave transmitted from the transmission device is reflected by the object, wherein
the transmission device and the reception devices are integrated into the substrate,
the transmission device is configured to transmit multiple ultrasonic waves having different frequencies, and
the circuit is configured to compensate for humidity based on the received ultrasonic waves having different frequencies.

2. The sensor according to claim 1, wherein
the transmission device transmits a first ultrasonic wave having a first frequency and a second ultrasonic wave having a second frequency,
the number of the reception devices is equal to or larger than three,
each of the transmission device and the three reception devices has a surface for transmitting or receiving the ultrasonic wave, the surface being perpendicular to a ground,
the three reception devices are composed of a first to a third reception devices,
the first reception device is disposed above the third reception device, and disposed on a left side of the second reception device,
the circuit calculates a horizontal plane distance between the object and the sensor in a horizontal plane parallel to the ground and a horizontal plane direction angle from the sensor to the object in the horizontal plane on the basis of the received ultrasonic waves having the first frequency received by the first and the second reception devices, and further calculates a vertical plane distance between the object and the sensor in a vertical plane perpendicular to the ground and a vertical plane direction angle from the sensor to the object in the vertical plane on the basis of the received ultrasonic waves having the first frequency received by the first and the third reception devices,
the circuit calculates a first attenuation loss between the transmitted ultrasonic wave and the received ultrasonic waves having the first frequency,
the circuit calculates a second attenuation loss between the transmitted ultrasonic wave and the received ultrasonic waves having the second frequency, and
the circuit calculates the humidity of environment on the basis of the first and the second attenuation losses and a temperature obtained from an external temperature sensor.

3. The sensor according to claim 1, further comprising:
a second transmission device for transmitting a second ultrasonic wave having a second frequency, which is different from a frequency of the ultrasonic wave transmitted from the transmission device.

4. The sensor according to claim 1, wherein the transmission device transmits multiple ultrasonic waves alternatively and periodically.

5. An ultrasonic sensor for detecting an object, comprising:
a substrate;
a transmission device for transmitting multiple ultrasonic waves having different frequencies;
a plurality of reception devices for receiving the ultrasonic waves, wherein the transmission device and the reception devices are integrated into the substrate,
means for processing received ultrasonic waves, which are received by the reception devices after the ultrasonic waves transmitted from the transmission device are reflected by the object, and for compensating for humidity based on an analysis of the received ultrasonic waves.

* * * * *